(12) United States Patent
Smith

(10) Patent No.: US 10,053,328 B2
(45) Date of Patent: Aug. 21, 2018

(54) ONE-WAY SNARE APPARATUS AND METHOD FOR ISOLATING A BROKEN ELASTIC STRAND

(71) Applicant: The Procter & Gamble Company, Cincinnati, OH (US)

(72) Inventor: Kevin Michael Smith, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/473,702

(22) Filed: Mar. 30, 2017

(65) Prior Publication Data
US 2017/0203936 A1 Jul. 20, 2017

Related U.S. Application Data

(63) Continuation of application No. 14/162,863, filed on Jan. 24, 2014, now Pat. No. 9,637,344.

(60) Provisional application No. 61/764,111, filed on Feb. 13, 2013.

(51) Int. Cl.
*B65H 63/024* (2006.01)
(52) U.S. Cl.
CPC .................. *B65H 63/024* (2013.01)
(58) Field of Classification Search
CPC ....... B65H 57/04; B65H 63/024; B65H 63/02
See application file for complete search history.

(56) References Cited

U.S. PATENT DOCUMENTS

| | | | |
|---|---|---|---|
| 3,860,003 | A | 1/1975 | Buell |
| 3,929,297 | A | 12/1975 | Zumfeld et al. |
| 4,180,118 | A | 12/1979 | Vecchiarelli |
| 4,274,607 | A | 6/1981 | Priest |
| 4,610,678 | A | 9/1986 | Weisman et al. |

(Continued)

FOREIGN PATENT DOCUMENTS

| EP | 1 410 778 A2 | 4/2004 |
|---|---|---|
| WO | WO 2014/120561 A1 | 8/2014 |

OTHER PUBLICATIONS

PCT International Search Report, PCT/US2014/012845, dated Apr. 15, 2014, 9 pages.

(Continued)

*Primary Examiner* — Michael C McCullough
(74) *Attorney, Agent, or Firm* — Charles R. Matson

(57) ABSTRACT

During the process of making elastomeric laminates, elastic material is advanced and stretched in a machine direction and may be joined with one or more substrates advancing in the machine direction. During the assembly process, one-way snare apparatuses and methods may be configured to automatically isolate elastic materials that may break. The one-way snares may include a housing and a snare member movably connected with the housing, wherein the snare member is movable relative to the housing between a first position and a second position. The one-way snares are adapted to permit advancement of continuous elastic strands in a first direction through the housing when the snare members are in the first position, and to prevent an end portion a broken elastic strand from retracting in a second direction through the housing when the snare member is in the second position, wherein the second direction is opposite the first direction.

5 Claims, 17 Drawing Sheets

(56) References Cited

U.S. PATENT DOCUMENTS

| | | |
|---|---|---|
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,167,897 A | 12/1992 | Weber et al. |
| 5,360,420 A | 11/1994 | Cook et al. |
| 5,562,646 A | 10/1996 | Goldman et al. |
| 5,599,335 A | 2/1997 | Goldman et al. |
| 5,628,097 A | 5/1997 | Benson et al. |
| 5,643,588 A | 7/1997 | Roe et al. |
| 5,669,894 A | 9/1997 | Goldman et al. |
| 5,674,216 A | 10/1997 | Buell et al. |
| 5,702,551 A | 12/1997 | Huber et al. |
| 5,916,661 A | 6/1999 | Benson et al. |
| 5,968,025 A | 10/1999 | Roe et al. |
| 6,107,537 A | 8/2000 | Elder et al. |
| 6,107,539 A | 8/2000 | Palumbo et al. |
| 6,118,041 A | 9/2000 | Roe et al. |
| 6,153,209 A | 11/2000 | Vega et al. |
| 6,410,129 B2 | 6/2002 | Zhang et al. |
| 6,426,444 B2 | 7/2002 | Roe et al. |
| 6,545,197 B1 | 4/2003 | Muller et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,790,798 B1 | 9/2004 | Suzuki et al. |
| 6,825,393 B2 | 11/2004 | Roe et al. |
| 6,861,571 B1 | 3/2005 | Roe et al. |
| 7,569,039 B2 | 8/2009 | Matsuda et al. |
| 9,637,344 B2* | 5/2017 | Smith ............... A61F 13/49009 |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2007/0131343 A1 | 6/2007 | Nordang |
| 2007/0219521 A1 | 9/2007 | Hird et al. |
| 2009/0312730 A1 | 12/2009 | LaVon et al. |
| 2011/0139657 A1 | 6/2011 | Hird et al. |
| 2011/0139658 A1 | 6/2011 | Hird et al. |
| 2011/0139659 A1 | 6/2011 | Hird et al. |
| 2011/0139662 A1 | 6/2011 | Hird et al. |
| 2011/0152812 A1 | 6/2011 | Hird et al. |
| 2012/0061015 A1 | 3/2012 | LaVon et al. |
| 2012/0061016 A1 | 3/2012 | LaVon et al. |
| 2013/0199696 A1 | 8/2013 | Schneider et al. |
| 2013/0199707 A1 | 8/2013 | Schneider et al. |
| 2013/0255861 A1 | 10/2013 | Schneider |
| 2013/0255862 A1 | 10/2013 | Schneider et al. |
| 2013/0255863 A1 | 10/2013 | Schneider et al. |
| 2013/0255864 A1 | 10/2013 | Schneider et al. |
| 2013/0255865 A1 | 10/2013 | Dean et al. |
| 2013/0277154 A1 | 10/2013 | Fritz et al. |
| 2014/0224855 A1 | 8/2014 | Smith |
| 2015/0090393 A1 | 4/2015 | Yanez et al. |

OTHER PUBLICATIONS

All Office Actions, U.S. Appl. No. 14/162,863.
All Office Actions, U.S. Appl. No. 14/162,831.

* cited by examiner

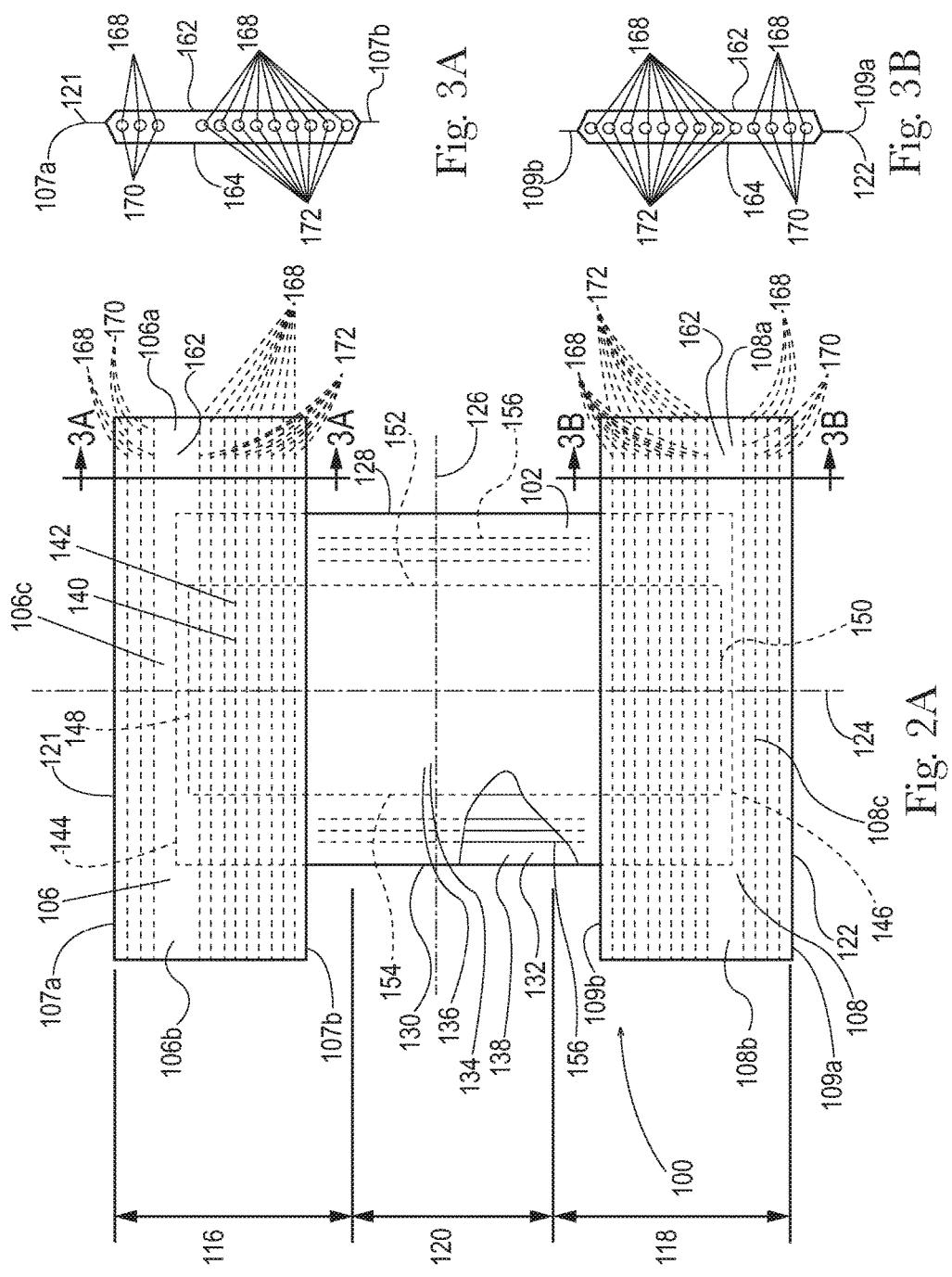

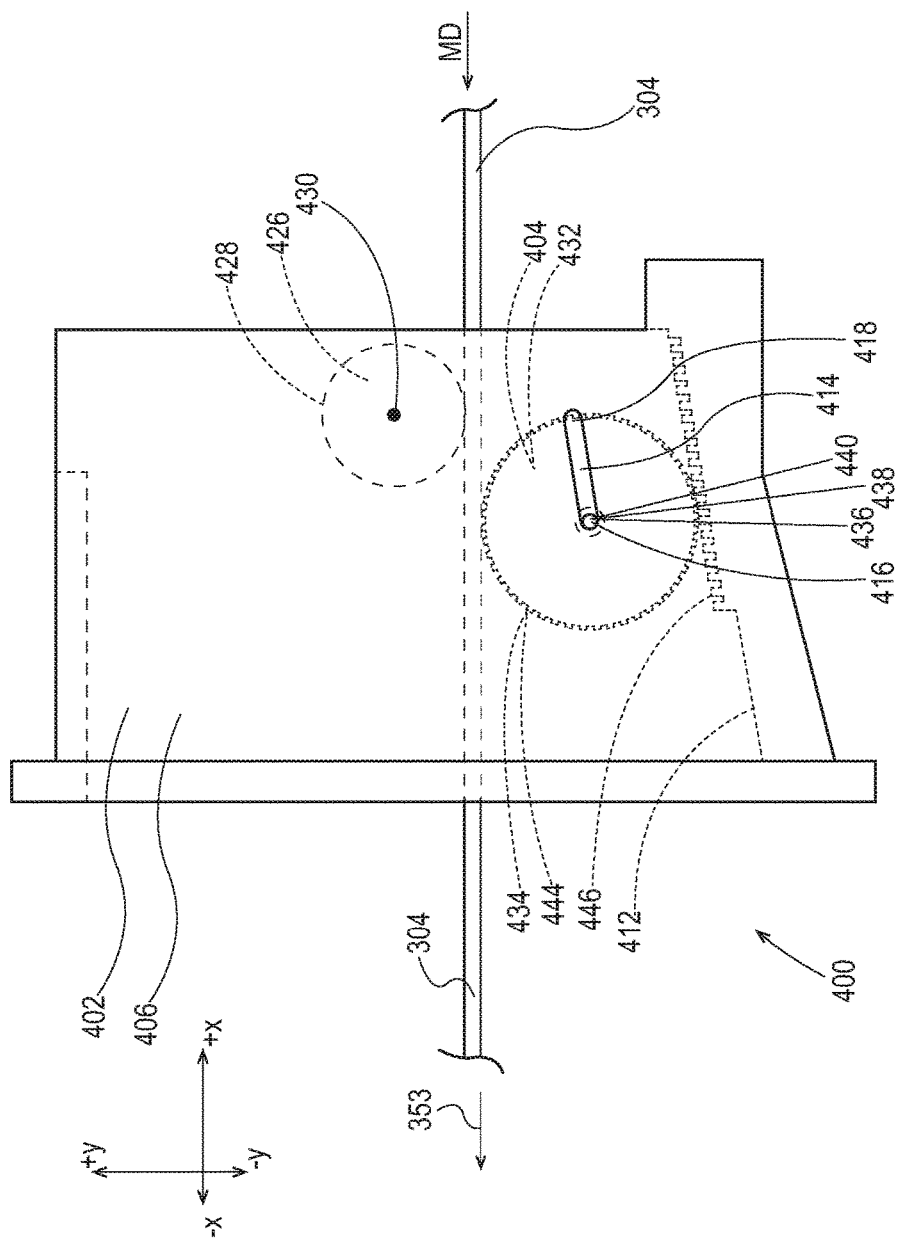

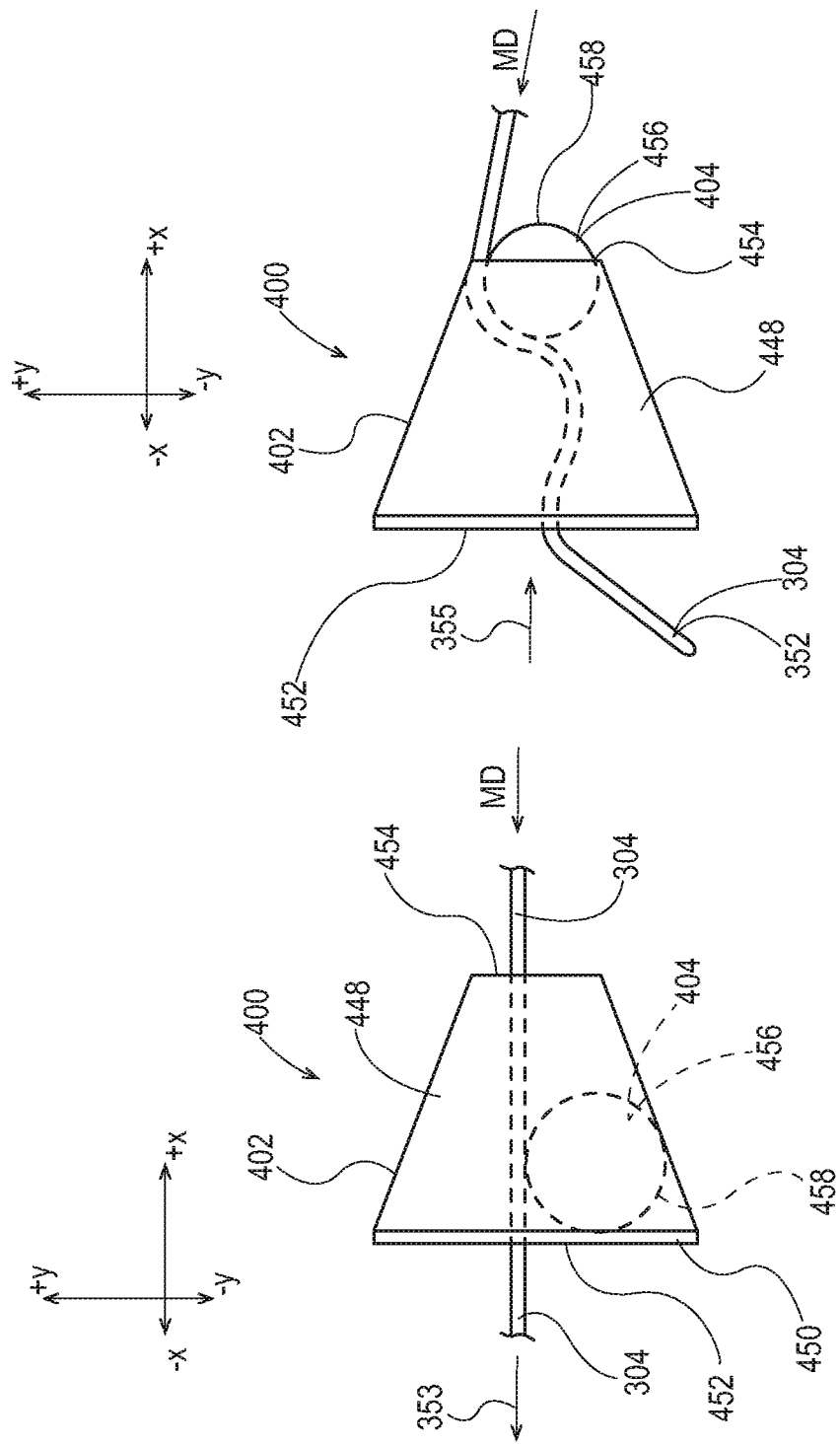

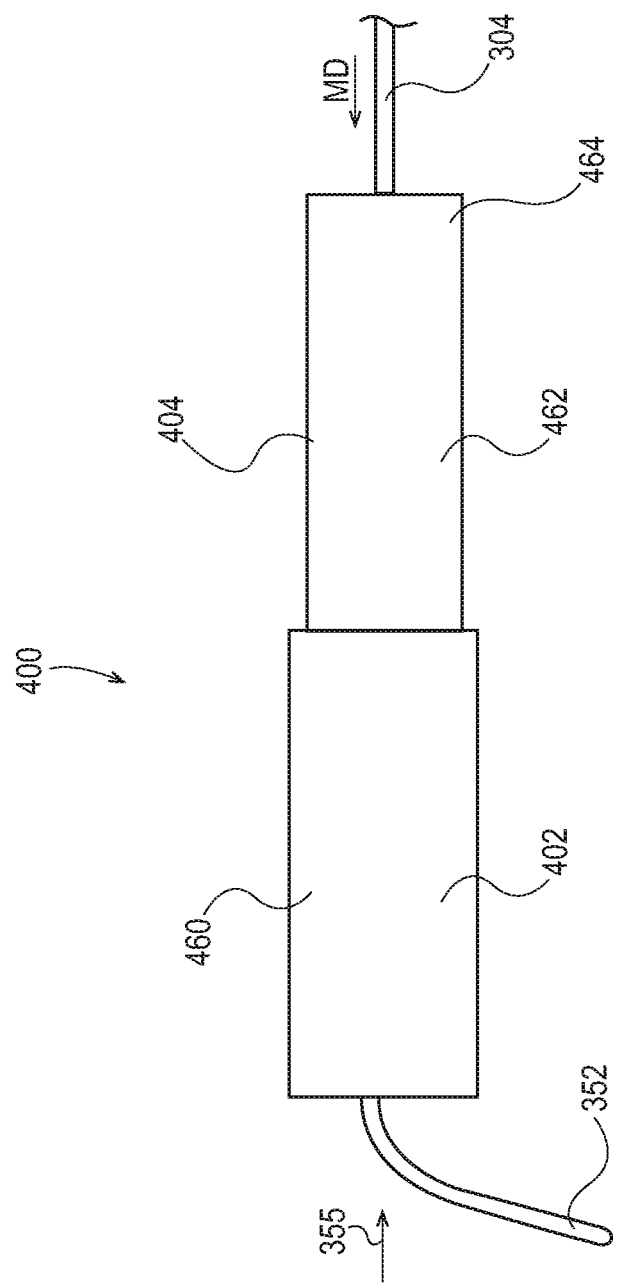

ONE-WAY SNARE APPARATUS AND METHOD FOR ISOLATING A BROKEN ELASTIC STRAND

FIELD OF THE INVENTION

The present disclosure relates to methods for manufacturing absorbent articles, and more particularly, to apparatuses and methods for making elastomeric laminates that may be used as components of absorbent articles.

BACKGROUND OF THE INVENTION

Along an assembly line, various types of articles, such as for example, diapers and other absorbent articles, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from an advancing web or webs are combined with other individual components created from other advancing webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers between the locations where the nonwoven is bonded to the elastic strands forming corrugations. The resulting elastomeric laminate is stretchable to the extent that the corrugations allow the elastic strands to elongate.

During the manufacture of elastic laminates, problems can be encountered in the manufacturing process when bonding elastic strands to substrates. For example, tensioned elastic strands may break during the assembly process. If a strand breaks under tension, a loose end of the broken strand may tend to snap back a significant distance toward an upstream portion of the manufacturing process. As such, the loose end may become entangled in other upstream manufacturing components, which in turn, may necessitate stopping the process in order to properly rethread the elastic strand to the intended position on the production machinery. In some configurations, several strands may advance through a manufacture process in close proximity to one another. Thus, a violent and uncontrolled retraction of a loose end of a broken strand may also cause additional strands to become broken. Consequently, it would be beneficial to provide a method and apparatus for producing an elastomeric laminate that is capable of automatically capturing and isolating upstream end portions of elastic strands that break during the production process to help reduce the amount of rethreading that would otherwise be necessary and to help reduce the likelihood of causing adjacent elastic strands in the process to become broken. Such methods and apparatus may also be used as a troubleshooting device to help identify the specific locations along the assembly line where elastic strands are breaking.

SUMMARY OF THE INVENTION

During the process of making elastomeric laminates, elastic material is advanced and stretched in a machine direction and may be joined with one or more substrates advancing in the machine direction. During the assembly process, one-way snare apparatuses and methods may be configured to automatically isolate elastic materials that may break. The one-way snares may include a housing and a snare member movably connected with the housing, wherein the snare member is movable relative to the housing between a first position and a second position. The one-way snares are adapted to permit advancement of continuous elastic strands in a first direction through the housing when the snare members are in the first position, and to prevent an end portion a broken elastic strand from retracting in a second direction through the housing when the snare member is in the second position, wherein the second direction is opposite the first direction.

In one form, a one way snare apparatus for isolating a broken elastic strand includes: a housing; a snare member connected with the housing, wherein the snare member is movable relative to the housing between a first position and a second position, wherein the snare member is movable in a first direction from the second position to the first position, and wherein the snare member is movable in a second direction from the first position to the second position; wherein when the snare member is in the first position, the snare member permits advancement of a continuous elastic strand in the first direction; and wherein when the snare member is in the second position, the snare member prevents an end portion of a broken elastic strand from retracting in the second direction through the housing, wherein the second direction is opposite the first direction.

In another form, an apparatus for isolating a broken elastic strand includes: a housing; a snare member movably connected with the housing, the snare member movable between a first position and a second position; a pathway extending through the housing adapted to receive an advancing elastic strand; wherein the pathway is relatively wide when the snare member is in the first position; and wherein the pathway is relatively narrow when the snare member is in the second position.

In yet another form, a method for isolating broken strands of elastic with a one way snare including a housing and a snare member movably connected with the housing, the method comprising the steps of: advancing an elastic strand in a first direction through the housing; placing the snare member in a first position; separating the elastic strand in the first direction to create an upstream end portion and a downstream end portion; retracting the upstream end portion in a second direction toward the housing, wherein the second direction is opposite the first direction; and capturing the upstream end portion by moving the snare member in the second direction to a second position.

BRIEF DESCRIPTION OF THE DRAWINGS

FIG. 2A is a partially cut away plan view of the diaper pant shown in FIG. 1.

FIG. 3A is a cross-sectional view of the diaper pants of FIGS. 2A and 2B taken along line 3A-3A.

FIG. 3B is a cross-sectional view of the diaper pants of FIGS. 2A and 2B taken along line 3B-3B.

FIG. 6C is a left side view of the one-way snare apparatus of FIG. 6A showing a snare member in a first position.

FIG. 7B is a left side view of the one-way snare apparatus of FIG. 7A showing a snare member in a first position.

FIG. 7C is a left side view of the one-way snare apparatus of FIG. 7A showing the snare member in a second position.

FIG. 8E is a left side view of the one-way snare apparatus of FIG. 8A showing the snare member in a second position.

DETAILED DESCRIPTION OF THE INVENTION

Figure 1:
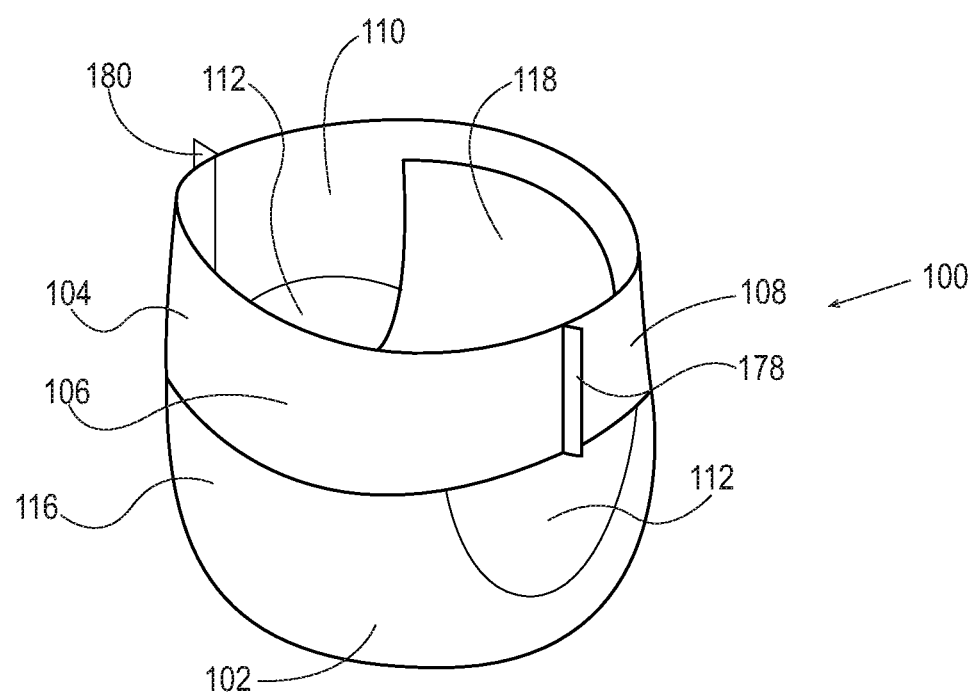
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The present disclosure relates to methods for manufacturing absorbent articles, and in particular, to methods for making elastomeric laminates that may be used as components of absorbent articles. The elastomeric laminates may include a first substrate, a second substrate, and an elastic material located between the first substrate and second substrate. During the process of making the elastomeric laminate, the elastic material may be advanced and stretched in a machine direction and may be joined with either or both the first and second substrates advancing in the machine direction. One-way snare apparatuses may be configured to automatically isolate elastic materials that may break during the assembly process. The one-way snares may include a housing and a snare member movably connected with the housing, wherein the snare member is movable relative to the housing between a first position and a second position. As discussed in more detail below, the one-way snares are adapted to permit advancement of continuous elastic strands in a first direction through the housing when the snare members are in the first position. The one-way snares are also adapted to prevent an end portion a broken elastic strand from retracting in a second direction through the housing when the snare member is in the second position, wherein the second direction is opposite the first direction. Thus, during the manufacture process, the snare member may be in the first position and stretched elastics strands may advance in a machine direction MD through the housing before being joined with a substrate. In the event that an elastic strand breaks, an upstream end portion of the elastic strand may retract back toward the housing, causing the snare member to move into the second position such that the upstream end portion is captured and isolated. As such, the snares may help prevent loose ends of the broken strands from snapping back a significant distance toward an upstream portion of the manufacturing process. In some manufacturing configurations where several strands may advance in close proximity to one another, the snares may help reduce the likelihood of a single broken strand causing adjacent elastic strands in the process to become broken. Further, snares may also be placed in various locations along a manufacturing line as a troubleshooting tool to help more easily identify the specific causes of and/or locations where elastic strands are breaking.

It is to be appreciated that the one-way snares may include housings and snare members configured in various ways to capture the retracting upstream end portions of broken elastic strands. For example, in some configurations, the snare member and housing may be configured such that when the snare member is the first position, a stretched elastic strand may advance in a first direction through the housing and past the snare member. When the elastic strand breaks, an upstream end portion of the broken elastic strand retracts in a second direction opposite the first direction toward the housing. The retracting upstream end portion causes the snare member to move in the second direction and into the second position. Once in the second position, the upstream end portion is pinched or compressed between the snare member and the housing, thus capturing and isolating the upstream end portion. In some example embodiments discussed below, the housing may include a bottom side, opposing side walls, and a cross member connected with and separating the side walls. And the snare member may be configured as a roller adapted to roll along the bottom side between the first and second positions. Opposing end portions of the roller may also be movably connected with the slots in the side walls. In other example embodiments, the housing may include a frustoconical shaped sidewall and a spherical shaped snare member, wherein the snare member is adapted to roll along the side wall between the first position and the second position.

In other configurations, the snare member and housing may be configured such that when the snare member is the first position, a stretched elastic strand may advance in a first direction through the snare member and through the housing. When the elastic strand breaks, an upstream end portion of the broken elastic strand retracts in a second direction opposite the first direction toward the housing. The retracting upstream end portion causes the snare member to move in the second direction and into the second position. Once in the second position, the upstream end portion is pinched or compressed within the snare member, thus capturing and isolating the upstream end portion. In some example embodiments discussed below, the housing may be configured as a first tube member, and the snare member may be configured as a second tube member telescopically received within the first tube member. The snare member may be adapted to define a first minimum internal diameter when in the first position, and to define a second minimum internal diameter when in the second position, wherein the first minimum internal diameter is greater than the second internal diameter.

As previously mentioned, the elastomeric laminates made according to the processes and apparatuses discussed herein may be used as to construct various types of components used in the manufacture of different types of absorbent articles. To help provide additional context to the subsequent discussion of the process embodiments, the following provides a general description of absorbent articles in the form of diapers that include components including the elastomeric laminates that may be produced with the methods and apparatuses disclosed herein.

FIGS. 1 and 2A show an example of a diaper pant 100 that may include components constructed from elastomeric laminates assembled in accordance with the apparatuses and methods disclosed herein. In particular, FIG. 1 shows a perspective view of a diaper pant 100 in a pre-fastened configuration, and FIG. 2A shows a plan view of the diaper pant 100 with the portion of the diaper that faces away from a wearer oriented towards the viewer. The diaper pant 100 shown in FIGS. 1 and 2A includes a chassis 102 and a ring-like elastic belt 104. As discussed below in more detail, a first elastic belt 106 and a second elastic belt 108 are connected together to form the ring-like elastic belt 104.

With continued reference to FIG. 2A, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 120 in the front waist region 116 and a longitudinally opposing and laterally extending back waist edge 122 in the back waist region 118. To provide a frame of reference for the present discussion, the diaper 100 and chassis 102 of FIG. 2A is shown with a longitudinal axis 124 and a lateral axis 126. In some embodiments, the longitudinal axis 124 may extend through the front waist edge 120 and through the back waist edge 122. And the lateral axis 126 may extend through a first longitudinal or right side edge 128 and through a midpoint of a second longitudinal or left side edge 130 of the chassis 102.

As shown in FIGS. 1 and 2A, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 120 in the front waist region 116 and the laterally extending back waist edge 122 in the back waist region 118. When the diaper pant 100 is worn on the lower torso of a wearer, the front waist edge 120 and the back waist edge 122 of the chassis 102 may encircle a portion of the waist of the wearer. At the same time, the chassis side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. patent application Ser. No. 13/435,503, entitled "METHODS AND APPARATUSES FOR MAKING LEG CUFFS FOR ABSORBENT ARTICLES", filed on Mar. 30, 2012.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1.

As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2A, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 120 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172.

As shown in FIG. 2A, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2A, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

Figure 2B:
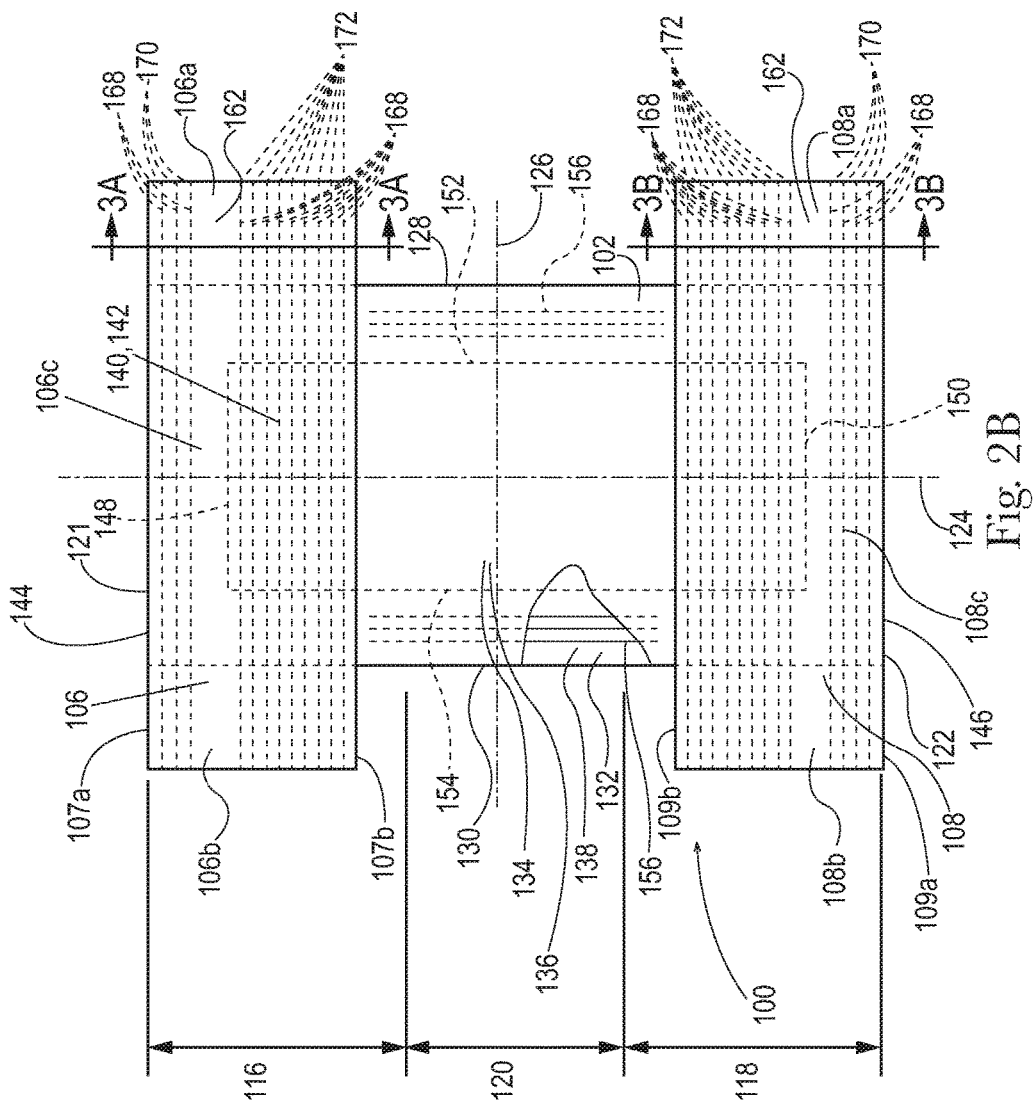
FIG. 2B is a partially cut away plan view of a second embodiment of a diaper pant.

It is to be appreciated that the chassis 102 and elastic belts 106, 108 may be configured in different ways other than as depicted in FIG. 2A. For example, FIG. 2B shows a plan view of a diaper pant 100 having the same components as described above with reference to FIG. 2A, except the first laterally extending end edge 144 of the chassis 102 is aligned along and coincides with the outer lateral edge 107a of the first elastic belt 106, and the second laterally extending end edge 146 is aligned along and coincides with the outer lateral edge 109a of the second belt 108.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

As previously mentioned, the apparatuses and methods according to the present disclosure may be utilized to assemble elastic laminates 302 used in various components of absorbent articles, such as for example, elastic belts 106, 108 and/or leg cuffs 156. Although the following methods may be provided in the context of the diaper 100 shown in FIGS. 1 and 2A, it is to be appreciated that the methods and apparatuses herein may be used to assemble various substrates and/or elastic laminates that can be used with various process configurations and/or absorbent articles, such as for example, disclosed in U.S. Pat. No. 7,569,039; U.S. Patent Publication Nos. US2005/0107764A1, US2012/0061016A1, and US2012/0061015A1; U.S. patent application Ser. No. 13/434,984, filed on Mar. 30, 2012; U.S. patent application Ser. No. 13/435,036, filed on Mar. 30, 2012; U.S. patent application Ser. No. 13/435,063, filed on Mar. 30, 2012; U.S. patent application Ser. No. 13/435,247, filed on Mar. 30, 2012; and U.S. patent application Ser. No. 13/435,503, filed on Mar. 30, 2012, all of which are incorporated by reference herein.

As previously mentioned, apparatuses and methods according to the present disclosure may be utilized to produce elastomeric laminates that may be used to construct various components of diapers 100, such as elastic belts, leg cuffs, and the like. For example, FIGS. 4A-5C show schematic views of converting apparatuses 300 adapted to manufacture elastomeric laminates 302. As described in more detail below, the converting apparatuses 300 shown in FIGS. 4A-5C operates to advance a continuous length of elastic material 304, a continuous length of a first substrate 306, and a continuous length of a second substrate 308 along a machine direction MD. The apparatus 300 stretches the elastic material 304 and joins the stretched elastic material 304 with the first and second substrates 306, 308 to produce an elastomeric laminate 302. Although the elastic material 304 is illustrated and referred to herein as strands, it is to be appreciated that elastic material 304 may include one or more continuous lengths of elastic strands, ribbons, and/or films.

The elastomeric laminates 302 can be used to construct various types of diaper components. For example, the elastomeric laminates 302 may be used as a continuous length of elastomeric belt material that may be converted into the first and second elastic belts 106, 108 discussed above with reference to FIGS. 1-3B. As such, the elastic strands 304 may correspond with the belt elastic material 168 interposed between the outer layer 162 and the inner layer 164, which in turn, may correspond with either the first and/or second substrates 306, 308. In other examples, the elastomeric laminates 306, 308 may used to construct waistbands in taped diaper configurations. Example taped diapers are disclosed in U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571. In yet other examples, the elastomeric laminates may be used to construct various types of leg cuff and/or topsheet configurations.

As discussed in more detail below, the converting apparatuses 300 may include metering devices arranged along a process machine direction MD, wherein the metering devices may be configured to stretch the advancing elastic material and/or join stretch elastic material with one or more advancing substrates. The converting apparatuses may also include one or more one-way snare apparatuses arranged between metering devices and adapted to capture and isolate broken elastic strands isolator apparatuses arranged between metering. During operation, elastic material may advance in a first direction from an upstream metering device, through the one-way snare, and to a downstream metering device. In the event that the stretched elastic material breaks while advancing from the upstream metering device to the downstream metering device, an upstream end portion of the broken elastic strand retracts in a second direction, opposite the first direction, toward the one-way snare. In turn, the one-way snare captures the upstream end portion of the broken elastic strand, preventing the upstream end portion from retracting further upstream.

Figure 4A:
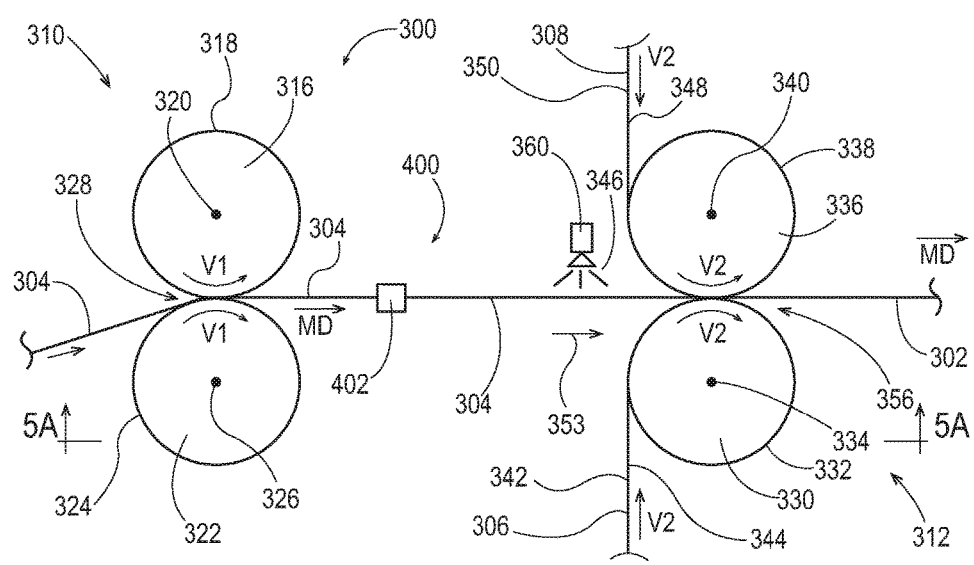
FIG. 4A is a schematic side view of a converting apparatus adapted to manufacture an elastic laminate including a first substrate, a second substrate, and elastic strands.
Figure 5A:
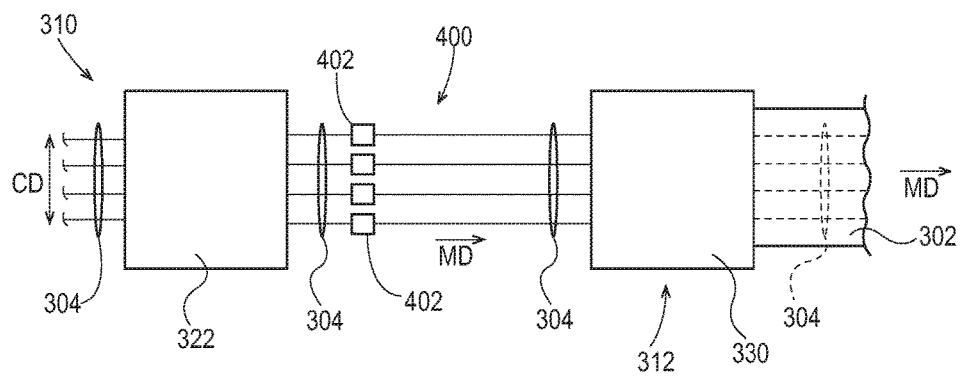
FIG. 5A is a view of the converting apparatus shown in FIG. 4A taken along line 5A-5A.

As shown in FIGS. 4A and 5A, a converting apparatus 300 for producing an elastic laminate 302 may include a first metering device 310, a second metering device 312, and a plurality of one-way snare apparatuses 400. Continuous elastic strands 304 advance in the machine direction MD from the first metering device 310, through the isolator apparatus 400, and to the second metering device 312. In addition, the elastic strands 304 may be stretched along the machine direction MD between the first and second metering devices 310, 312. The stretched elastic strands 304 are also joined with a first substrate 306 and a second substrate 308 at the second metering device 312 to produce an elastomeric laminate 302. It is to be appreciated that different components may be used to construct the elastomeric laminates 302 in accordance with the methods and apparatuses herein. For example, the first and/or second substrates 306, 308 may include nonwovens and/or films. It is also to be appreciated that although FIGS. 4A and 5A show four elastic strands 304 advancing through four separate one-way snares 400, it is to be appreciated that the apparatuses herein may be configured such more or less than four elastic strands 304 advance through more or less than four one-way snares 400, and/or that additional one-way snares 400 may be arranged along the cross direction CD of a converting process and/or arranged along a machine direction MD in various different portions of a converting process.

As shown in FIGS. 4A and 5A, the first metering device 310 may include: a first roller 316 having an outer circumferential surface 318 and rotates about a first axis of rotation 320, and a second roller 322 having an outer circumferential surface 324 and rotates about a second axis of rotation 326. The first roller 316 and the second roller 322 rotate in opposite directions, and the first roller 316 is adjacent the second roller 322 to define a first nip 328 between the first roller 316 and the second roller 322. The first roller 316 rotates such that the outer circumferential surface 318 has a surface speed V1, and the second roller 322 may rotate such that the outer circumferential surface 324 also has the same, or substantially the same, surface speed V1. The second metering device includes: a third roller 330 having an outer circumferential surface 332 and rotates about a third axis of rotation 334, and a fourth roller 336 having an outer circumferential surface 338 and rotates about a fourth axis of rotation 340. The third roller 330 and the fourth roller 336 rotate in opposite directions, and the third roller 330 is adjacent the fourth roller 336 to define a second nip 356 between the third roller 330 and the fourth roller 336. The third roller 330 rotates such that the outer circumferential surface 332 has a surface speed V2, and the fourth roller 336 may rotate such that the outer circumferential surface 338 has the same, or substantially the same, surface speed V2, wherein V2 is greater than V1.

As shown in FIGS. 4A and 5A, the first substrate 306 includes a first surface 342 and an opposing second surface 344, and the first substrate 306 advances at speed V2 in the machine direction MD to the third roller 330. In particular, the first substrate 306 advances in the machine direction MD at speed V2 to the third roller 330 where the first substrate 306 partially wraps around the outer circumferential surface 332 of the third roller 330 and advances through the second nip 356. As such, the second surface 344 of the first substrate 306 travels in the same direction as and in contact with the outer circumferential surface 332 of the third roller 330. In addition, the second substrate 308 includes a first surface 348 and an opposing second surface 350, and the second substrate 308 advances at speed V2 in the machine direction MD to the fourth roller 336. In particular, the second substrate 308 advances in the machine direction MD at speed V2 to the fourth roller 336 where the second substrate 308 partially wraps around the outer circumferential surface 338 of the fourth roller 336 and advances through the second nip 356. As such, the first surface 348 of the second substrate 308 travels in the same direction as and in contact with the outer circumferential surface 338 of the fourth roller 336.

With continued reference to FIGS. 4A and 5A, the elastic strands 304 advance in the machine direction MD through the first nip 328 to the second nip 356. Upstream of the first nip 328, the elastic strands 304 may advance at speed V1 or less. From the first nip 328, the elastic strands 304 advance to the second nip 356 where the elastic strands 304 are joined with the first and second substrates 306, 308. Because the elastic strands 304 are advancing at speed V1 at the first nip 328 and is advancing at speed V2 at the second nip 356, wherein V2 is greater than V1, the elastic strands 304 are stretched in the machine direction MD between the first nip 328 and the second nip 356. In turn, the stretched elastic strands 304 advance through the second nip 356 between the first and second substrates 306, 308 such that the elastic material is joined with the first surface 342 of the first substrate 306 and the second surface 350 of the second substrate 308 to produce a continuous length of elastomeric laminate 302. As shown in FIG. 4A, the elastic strands 304 may advance past an adhesive applicator device 360 that applies adhesive 346 to the elastic strands 304 before advancing to the second nip 356. It is to be appreciated that adhesive may also be applied to the first surface 342 of the first substrate 306 before and/or while being joined with the elastic strands 304 and/or the second substrate 308. In addition, it is to be appreciated that adhesive may be applied to the second surface 350 of the second substrate 308 before or while being joined with the elastic strands 304 and first substrate 306.

Figure 4B:
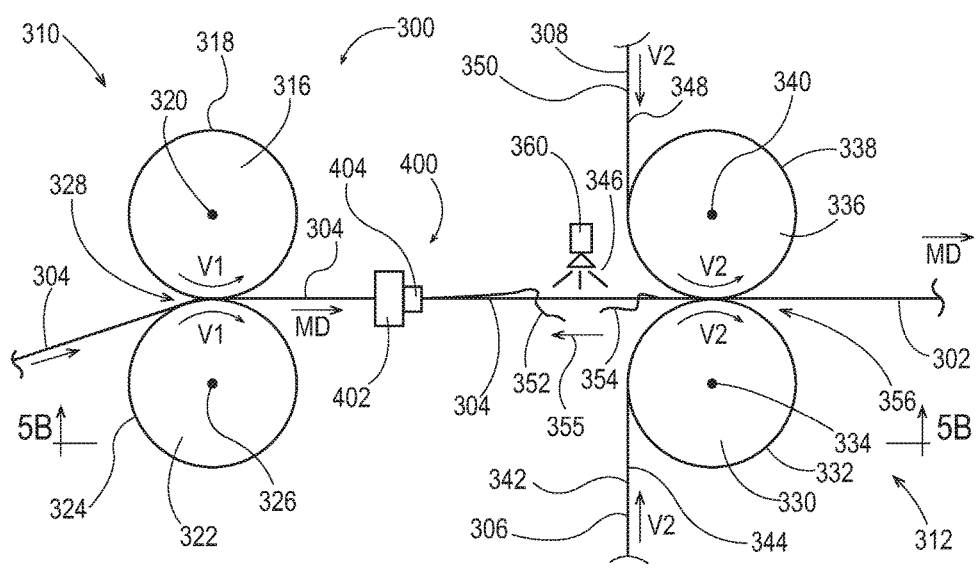
FIG. 4B is a schematic side view of the converting apparatus shown in FIG. 4A showing a broken elastic strand.
Figure 5B:
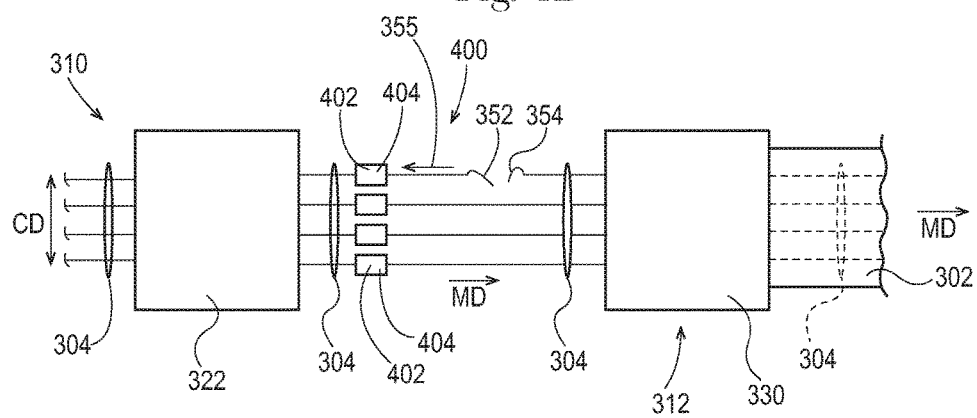
FIG. 5B is a view of the converting apparatus shown in FIG. 4B taken along line 5B-5B.
Figure 4C:
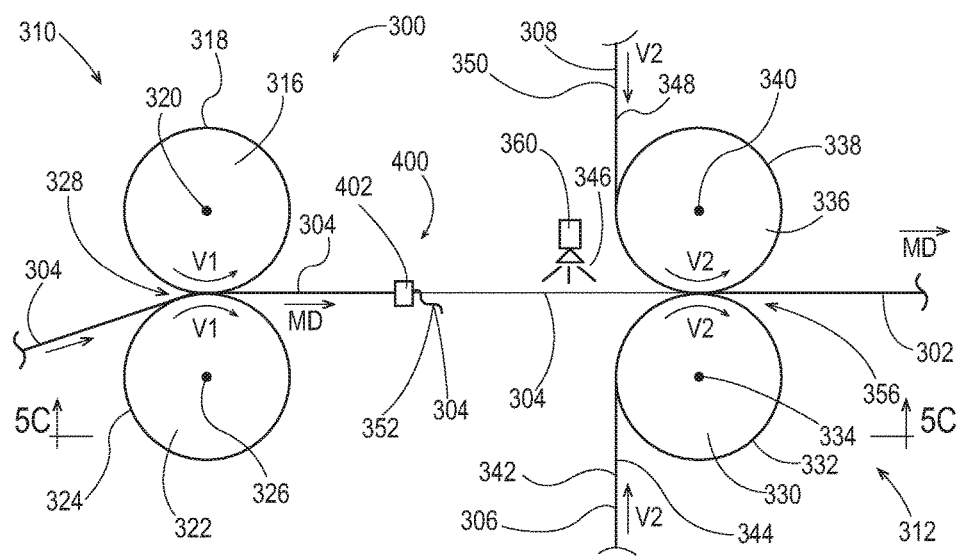
FIG. 4C is a schematic side view of the converting apparatus shown in FIG. 4B showing an upstream end portion of the broken elastic strand captured by a one-way snare.
Figure 5C:
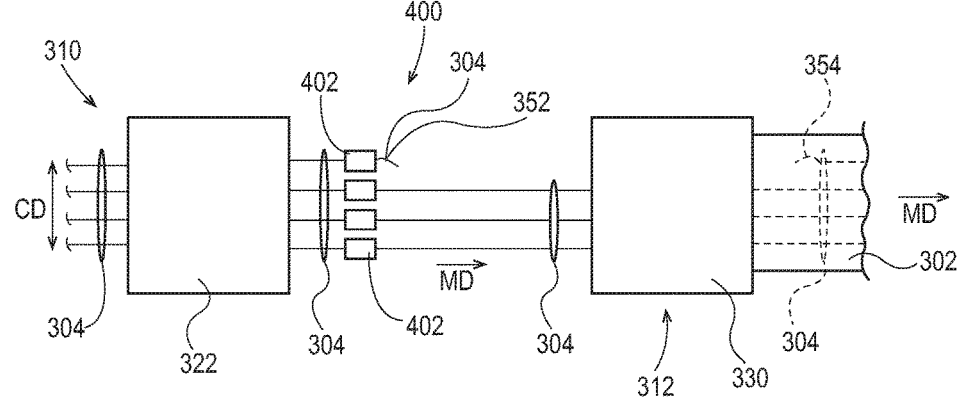
FIG. 5C is a view of the converting apparatus shown in FIG. 4C taken along line 5C-5C.

As previously mentioned, the elastic strands 304 may break while the apparatus 300 is producing an elastomeric laminate 302. FIGS. 4A-5C illustrate a sequence wherein a single elastic strand 304 breaks and is captured by the one-way snare apparatus 400. As described above, FIGS. 4A and 5A shows the apparatus 300 operating to produce an elastomeric laminate 302 with four elastic strands 304 being stretched between the first metering device 310 and the second metering device 312. FIGS. 4B and 5B show a state wherein one of the elastic strands 304 has broken or separated in the machine direction MD between the first nip 328 and the second nip 356, thus creating an upstream end portion 352 and a downstream end portion 354. Because the elastic material is being stretched between the first nip and the second nip, the downstream end portion 354 may snap back in a downstream direction toward the second nip 356, and the upstream end portion 352 may snap back in an upstream direction toward the first nip 328 and the one-way snare 400. More particularly, as shown in FIG. 4A, the elastic strands 304 are advancing in a first direction 353, which may be referred to as a machine direction MD. And as shown in FIGS. 4B-5B, the upstream end portion 352 of the broken elastic strand 304 snaps back in a second direction 355 that is opposite the first direction 353 toward the one-way snare 400. As shown in FIGS. 4B-5C, the downstream end portion 354 of the broken elastic strand 304 continues to advance in the machine direction MD through the second nip 356 and is incorporated into the elastomeric laminate 302. As previously mentioned, the upstream end portion 352 of the broken elastic strand 304 may snap back toward the first nip 328 and become captured by the one-way snare 400, such as shown in FIGS. 4C and 5C.

As discussed in more detail below, the one-way snare apparatuses 400 herein may include a housing 402 and a snare member 404 movably connected with the housing 402. In operation, such as shown in FIGS. 4A-5C, the one-way snares 400 permit advancement of continuous elastic strands 304 in the first direction 353 through the housing 402 when the snare member is in a first position. However, the one-way snares 400 are also configured to prevent the upstream end portion 352 of the broken elastic strand 304 from retracting in the second direction 355 through the housing 402 and toward the first nip 328 when the snare member is in a second position. As such, stretched elastics strands 304 may advance in a machine direction MD through the housing 402 before being joined with the first and second substrates 306, 308. In the event that an elastic strand 304 breaks, the upstream end portion 352 may retract back toward the housing 402 and is captured and isolated when the snare member 404 moves from the first position to the second position.

It is to be appreciated that the one way snare apparatuses 400 herein may be configured in various different ways to capture upstream end portions of broken elastic material. For example, FIGS. 6A-6D show an example one-way snare 400 that includes a housing 402 and a snare member 404. As discussed below, the snare member 404 is connected with the housing 402 such that the snare member 404 is adapted to move between a first position and a second position. The housing 402 includes a first side wall 406, a second side wall 408, a top side 410, and a bottom side 412. The first side wall 406 includes a first slot 414 having a first end portion 416 and a second end portion 418, and the second side wall 408 includes a second slot 420 having a first end portion 422 and a second end portion 424. The housing 402 also includes a cross member 426 connected with the first wall 406 and the second wall 408. The cross member 426 includes an outer circumferential surface 428 and may be adapted to rotate about an axis of rotation 430. In some configurations, the cross member 426 may be configured as a stationary member, such as a bar that does not rotate.

Figure 6A:
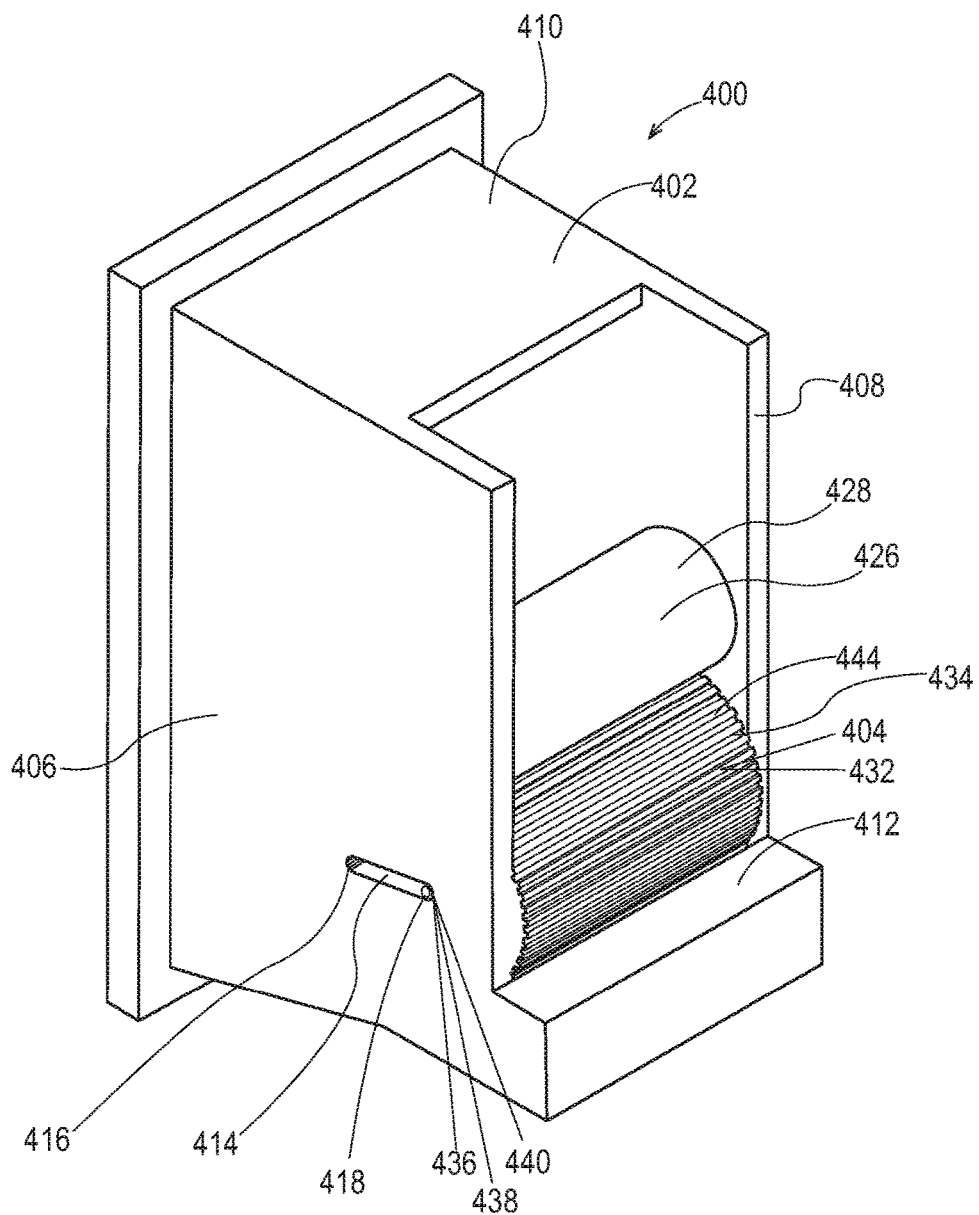
FIG. 6A is a front isometric view of a first embodiment of a one-way snare apparatus.
Figure 6B:
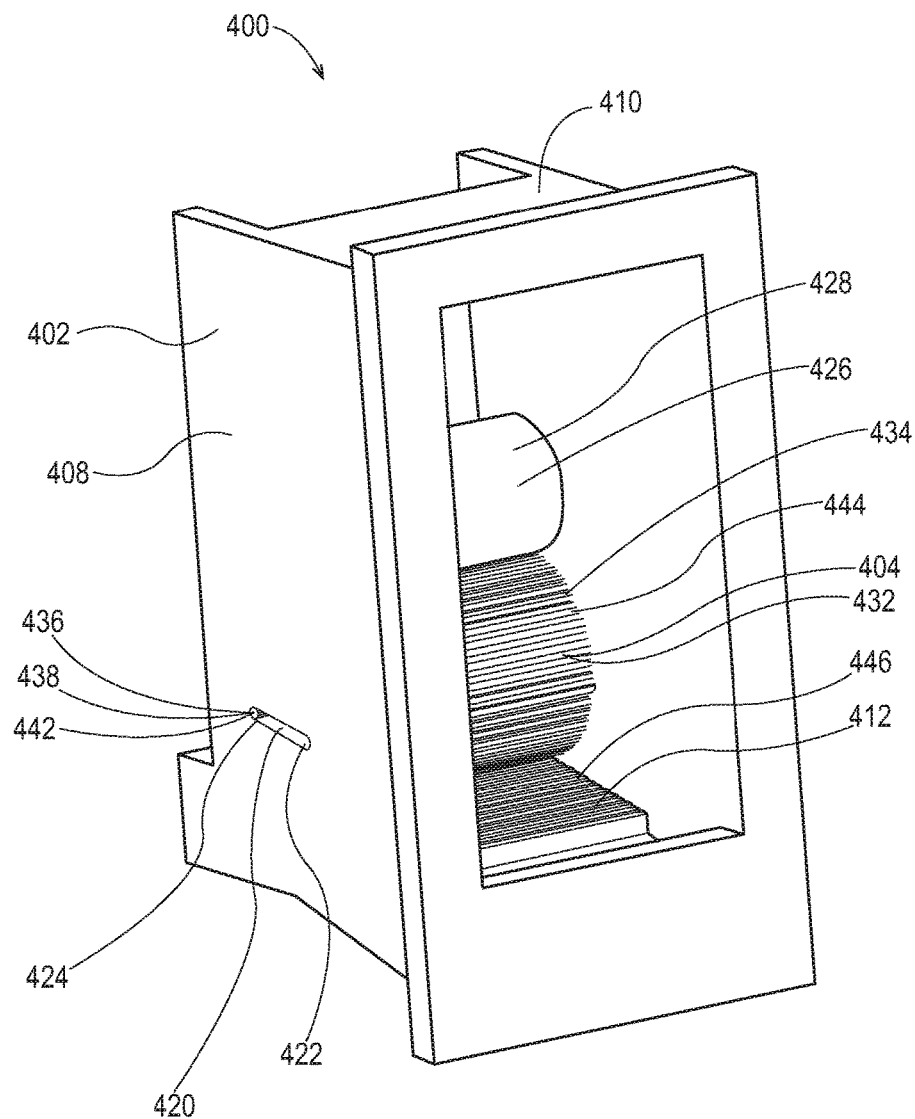
FIG. 6B is a rear isometric view of the one-way snare apparatus shown in FIG. 6A.
Figure 6D:
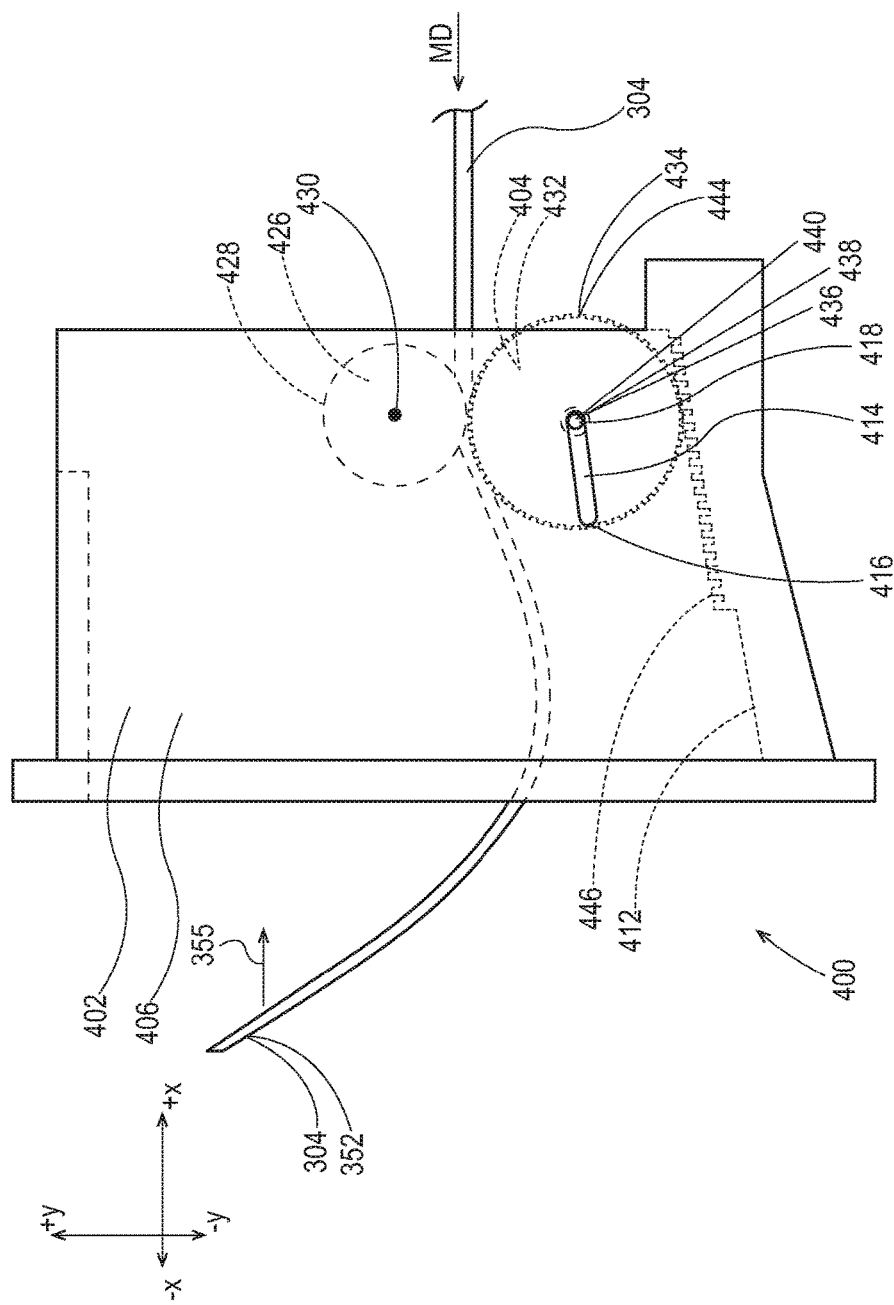
FIG. 6D is a left side view of the one-way snare apparatus of FIG. 6A showing the snare member in a second position.

With continued reference to FIGS. 6A-6D, the snare member 404 may be configured as a cylindrically-shaped roller 432. The roller includes an outer circumferential surface 434 and is adapted to rotate about an axis of rotation 436. The roller may also include an axle 438 having a first end portion 440 and an opposing second end portion 442. The first end portion 440 of the axle 438 may be connected with and adapted to move along the length of the first slot 414, and the second end portion 442 of the axle 438 may be connected with and adapted to move along the length of the second slot 420. As shown in FIG. 6C, the snare member 404 may be in placed in the first position when the first and second end portions 440, 442 of the axle 438 are moved toward the first end portions 416, 422 of the first and second slots 414, 422. And as shown in FIG. 6D, the snare member 404 may be placed in the second position when the first and second end portions 440, 442 of the axle 438 are moved toward the second end portions 418, 424 of the first and second slots 414, 422. As shown in FIGS. 6C and 6D, the outer circumferential surface 434 of the snare member 404 may also be in contact with and rollingly connected with the bottom side 412 of the housing 402. As such, the roller 432 may roll along the bottom side 412 as the snare member 404 moves between the first and second positions. In addition, the outer circumferential surface 434 of the roller 432 may include teeth 444 adapted to mesh with the teeth 446 of on the bottom side 412 of the housing 402.

An x-y axis coordinate system 500 is provided in FIGS. 6C and 6D to help provide additional reference to the description of the one-way snare 400. As shown in FIGS. 6C and 6D, the one-way snare may also be configured such that the bottom side 412, the first slot 414, and the second slot 420 are sloped to have −x and −y directional components along the MD direction. Thus, the snare member 404 travels in +x and +y directions when moving from the first position (such as shown in FIG. 6C) to the second position (such as shown in FIG. 6D). With respect to FIGS. 6C and 6D, the outer circumferential surface 428 of the cross member 426 is separated from the outer circumferential surface 434 of the roller 432 by a first minimum distance when the snare member 404 is in the first position; and the outer circumferential surface 428 of the cross member 426 is separated from the outer circumferential surface 434 of the roller 432 by a second minimum distance when the snare member 404 is in the second position, wherein the first minimum distance is greater than the second minimum distance.

FIG. 6C shows the snare member 404 in the first position, wherein an elastic strand 304 is permitted to advance in the first direction 353, which may also be referred to as the machine direction MD, through the housing 402 and past the snare member 404. In particular, the elastic strand 304 advances in the first direction 353 between the first and second side walls 406, 408 of the housing 402. The elastic strand 304 is also permitted to advance in the first direction 353 between the outer circumferential surface 428 of the cross member 426 and the outer circumferential surface 434 of the roller 432. In the event that an elastic strand 304 breaks, an upstream end portion 352 of the broken strand 304 snaps back in the second direction 355 toward the one-way snare 400. As the upstream end portion 352 retracts in the second direction 355, the elastic strand 304 pulls the snare member 404 from the first position (such as shown in FIG. 6C) to the second position (such as shown in FIG. 6D).

As the snare member moves from the first position to the second position, the roller 432 rolls along the bottom side 412 of the housing 402 and the first and second end portions 440, 442 of the axle 438 travels the second end portions 418, 424 of the first and second slot 414, 420. In turn, the outer circumferential surface 434 of the roller 432 moves closer to the outer circumferential surface 428 of the cross member 426 until the upstream end portion 352 becomes wedged and captured between the outer circumferential surface 428 of the cross member 426 and the outer circumferential surface 434 of the roller 432. Thus, the one-way snare 400 prevents the upstream end portion 352 of the broken elastic strand 304 from retracting further upstream in the manufacturing process. Once the broken elastic strand is detected, the broken strand can be rethreaded through the manufacturing process from the location of capture by the one-way snare 400.

Figure 7A:
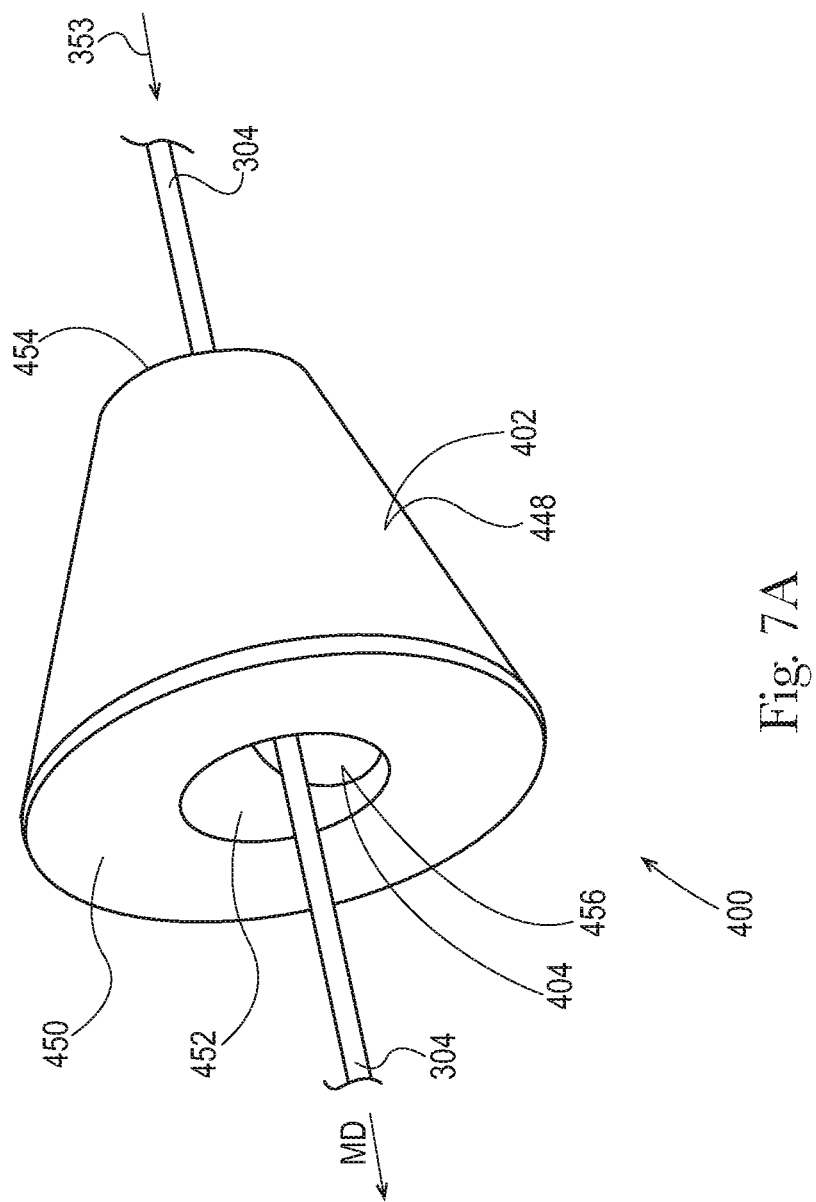
FIG. 7A is a rear isometric view of a second embodiment of a one-way snare apparatus.

As mentioned above, it is to be appreciated that the one-way snare 400 may be configured with various types of housings 402 and snare members 404 adapted to capture the upstream end portions 352 of broken elastic strands 304. For example, FIGS. 7A-7C show a second embodiment of a one-way snare apparatus 400 including a housing 402 and a snare member 404. The housing 402 includes a frustoconical shaped side wall 448 and first end wall 450. A first end opening 452 may be defined in the disc-shaped first end wall 450, and an opposing second end opening 454 may be defined by the sidewall 448. The snare member 404 may be configured as a spherical shaped or ball shaped member 456 having an outer circumferential surface 458. The one-way snare is configured such that the spherical shaped member 456 cannot pass through the second end opening 454. For example, the spherical shaped member 456 may be defined by a first diameter, and the second end opening 454 may be defined by a second diameter that is smaller than the first diameter. As discussed below, the snare member 404 is adapted to roll along the side wall 448 from a first position to a second position between the first end opening 452 and the second end opening 454.

An x-y axis coordinate system 500 is provided in FIGS. 7B and 7C to help provide additional reference to the description of the one-way snare 400. As shown in FIGS. 7C and 7D, the snare member 404 travels in +x and +y directions when moving from the first position (such as shown in FIG. 7B) to the second position (such as shown in FIG. 7C). With respect to FIGS. 7B and 7C, the outer circumferential surface 458 of the spherical shaped member 456 may be in contact with the first end wall 450 and the side wall 448 when the snare member 404 is in the first position; and the outer circumferential surface 458 of the spherical shaped member 456 may block the second end opening when the snare member 404 is in the second position.

FIG. 7B shows the snare member 404 in the first position, wherein an elastic strand 304 is permitted to advance in the first direction 353, which may also be referred to as the machine direction MD, through the housing 402 and past the snare member 404. In particular, the elastic strand 304 advances in the first direction 353 through second end opening 454, the sidewall 448, and the first end opening 452. The elastic strand 304 is also permitted to advance in the first direction 353 past the outer circumferential surface 458 of the spherical shaped member 456. In the event that an elastic strand 304 breaks, an upstream end portion 352 of the broken strand 304 snaps back in the second direction 355 toward the one-way snare 400. As the upstream end portion 352 retracts in the second direction 355, the elastic strand 304 pulls the snare member 404 from the first position (such as shown in FIG. 7B) to the second position (such as shown in FIG. 7C). As the snare member moves from the first position to the second position, the spherical shaped member 456 rolls along the sidewall 448 toward the second end opening 454. In turn, the outer circumferential surface 458 of the spherical shaped member moves closer to the perimeter of the second end opening 454 until the upstream end portion 352 becomes wedged and captured between the outer circumferential surface 458 of the spherical shaped member 456 and a portion of the sidewall 448 that defines the perimeter second end opening 454. Thus, the one-way snare 400 prevents the upstream end portion 352 of the broken elastic strand 304 from retracting further upstream in the manufacturing process.

FIGS. 8A-8E show a third embodiment of a one-way snare apparatus 400 including a housing 402 and a snare member 404. The housing 402 includes a first tube member 460. And the snare member 404 may be configured as a second tube member 462 adapted to be telescopically received within the first tube member 460. As discussed below, the snare member 404 is adapted to move along the inside of the first tube member 460 from a first position to a second position. When in the snare member 404 is in the first position, a stretched elastic strand 304 may advance in a first direction 353 through the first tube member 460 and through the second tube member 462. When the elastic strand 304 breaks, an upstream end portion 352 of the broken elastic strand retracts in a second direction 355 opposite the first direction 353 toward the housing 402. The retracting upstream end portion 352 causes the snare member 404 to move within the first tube member 460 in the second direction 355 and into the second position. Once in the second position, the upstream end portion 352 of the elastic strand 304 is pinched or compressed within the second tube member 462, thus capturing and isolating the upstream end portion.

Figure 8A:
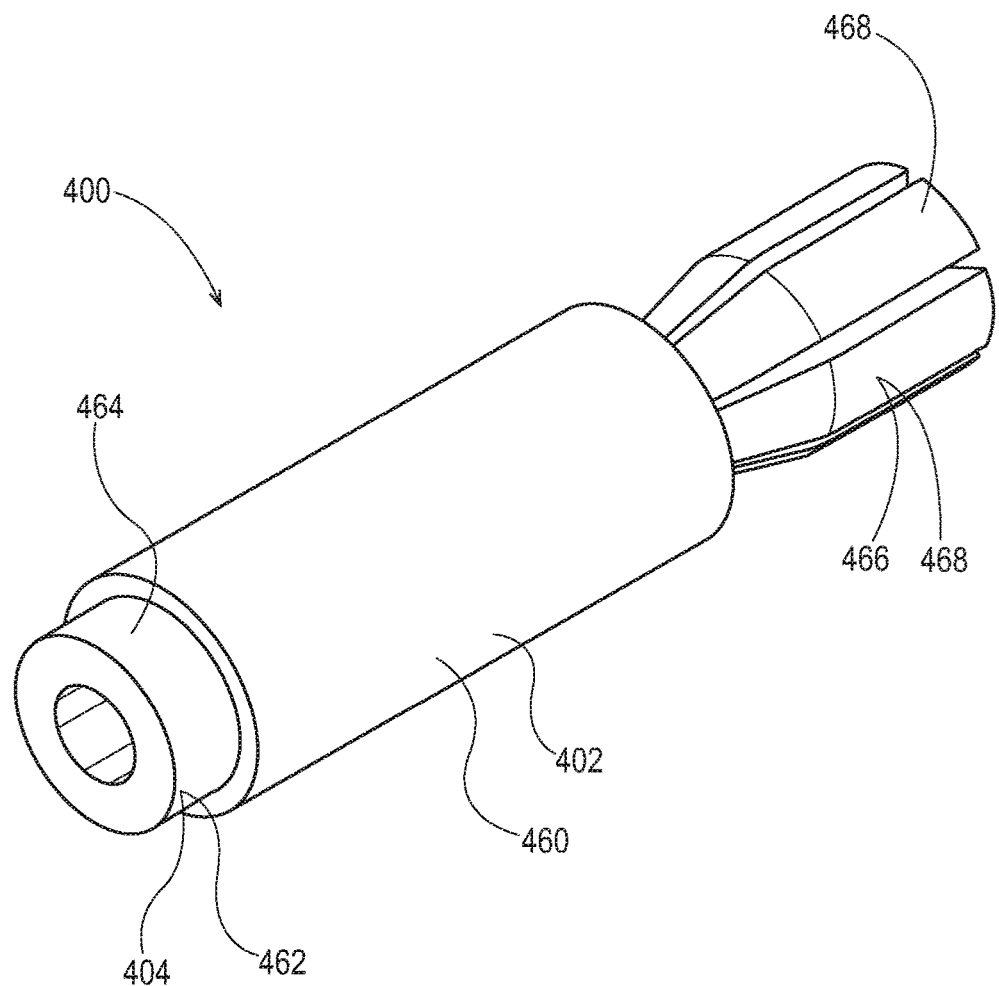
FIG. 8A is a front isometric view of a third embodiment of a one-way snare apparatus.
Figure 8B:
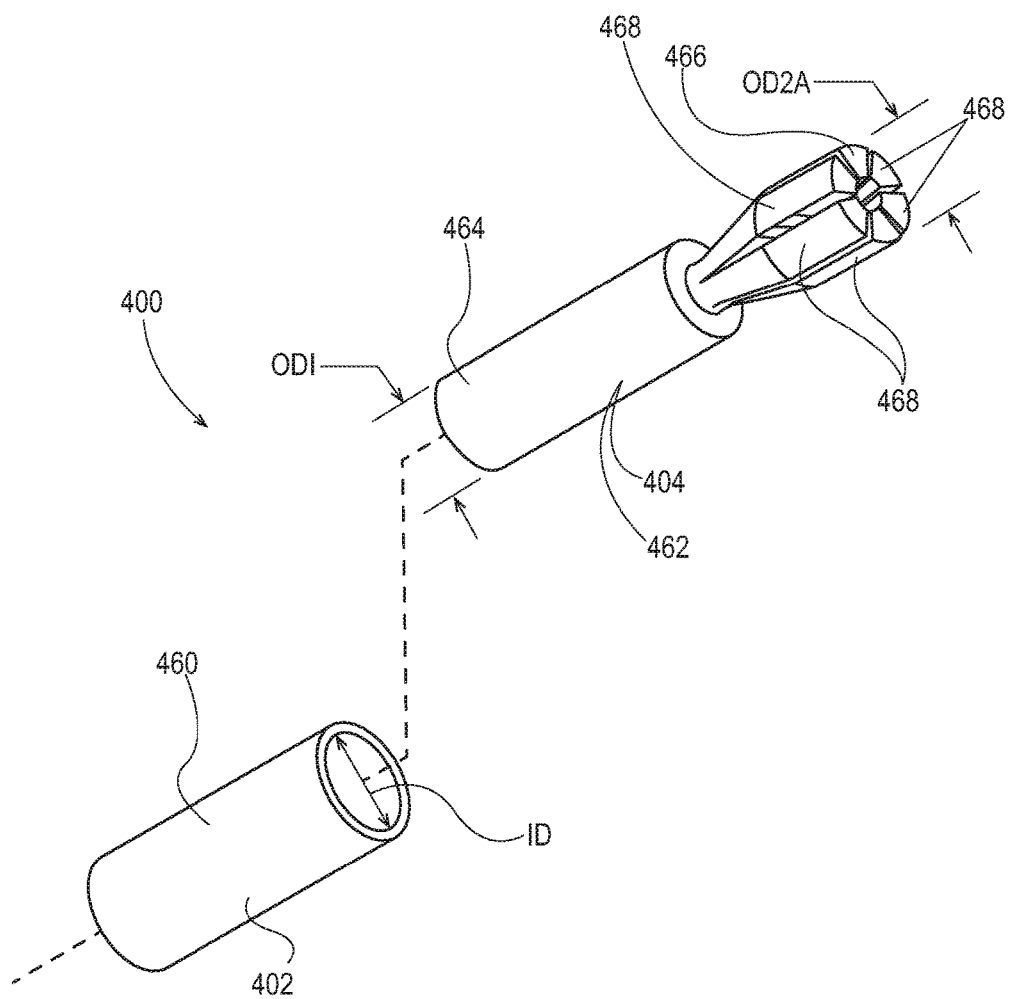
FIG. 8B is an exploded view of the one-way snare apparatus of FIG. 8A.

As previously mentioned, the second tube member 462 is telescopically received within the first tube member 460. As shown in FIGS. 8A and 8B, the second tube member 462 includes a cylindrically shaped first end portion 464 having an outer diameter, OD1, that is slightly smaller than an inner diameter, ID, of the first tube member 460, such that the second tube member 462 can move back and forth along the inside length of the first tube member 460. The second tube member 462 also includes a second end portion 466 with a plurality of compression members 468 that define an outer diameter, OD2A. The outer diameter OD2A may also be slightly smaller than the inner diameter ID of the first tube member 460. As discussed below, the snare member 404 may be configured such that an elastic strand 304 advances through the second tube member 462 from the first end portion 464 and to the second end portion 466. A portion of the elastic strand advancing through the second end portion 466 forces the compression members 468 radially outward from the elastic strand 304, such as indicated by directional arrows A in FIG. 8D. The radial outward movement of the compression members 468 increases the outer diameter of the second end portion 466 from OD2A (such as shown in FIG. 8B) to a relatively larger outer diameter OD2B (such as show in FIG. 8D).

Figure 8C:
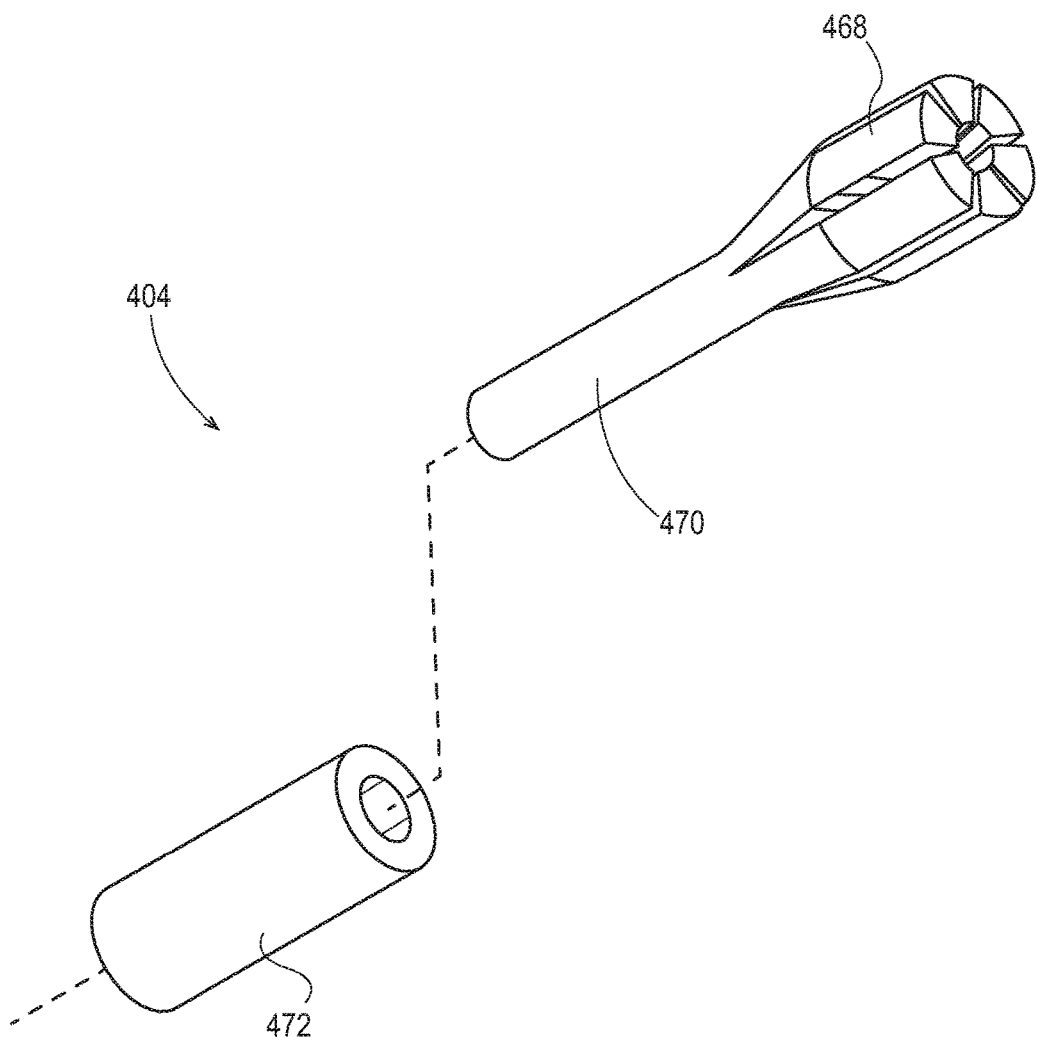
FIG. 8C is an exploded view of the snare member of FIG. 8B

It is to be appreciated that the second tube member 462 may be configured in various ways. In some configurations, the second tube member 462 may be constructed from more than parts. For example, as shown in FIG. 8C, the second tube member 462 may include a compression tube 470 connected with a sleeve 472. In other configurations, the second tube member 462 may be a unitary construction.

During operation, the snare member 404 may be in a first position wherein the compression members 468 are located outside of the first tube member 460 or are otherwise not acted on by the housing 402. When in the first position, elastic strand 304 is permitted to advance in the first direction 353, which may also be referred to as the machine direction MD, through the housing 402 and through the snare member 404. In particular, the elastic strand 304 advances through the second tube member 462 from the first end portion 464 to the second end portion 466. And as the elastic strand 304 advances through the second end portion 466, the compression members are forced outward such that the outer diameter of the second end portion 466 increases from OD2A, shown in FIG. 8C, to a larger outer diameter OD2B, show in FIG. 8D. In addition, the outer diameter OD2B may be larger than the inner diameter of the first tube member 460.

Figure 8D:
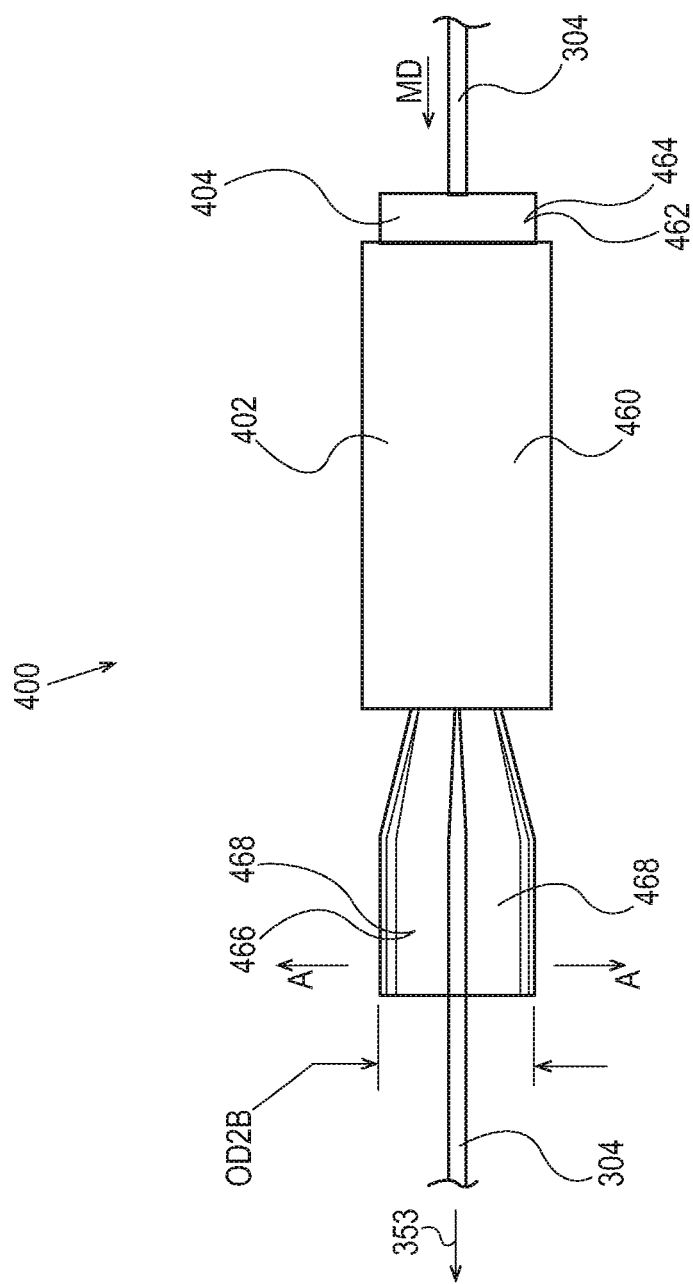
FIG. 8D is a left side view of the one-way snare apparatus of FIG. 8A showing the snare member in a first position.

In the event that an elastic strand 304 breaks, an upstream end portion 352 of the broken strand 304 snaps back in the second direction 355 toward the one-way snare 400. As the upstream end portion 352 retracts in the second direction 355, the elastic strand 304 pulls the snare member 404 from the first position (such as shown in FIG. 8D) to the second position (such as shown in FIG. 8E). In particular, the second end portion 466 and associated compression members 468 of the second tube member 462 move into the first tube member 460. Thus, as the snare member 404 moves from the first position to the second position, the relatively smaller inner diameter ID of the first tube member 460 interferes with the relatively larger outer diameter OD2B of the second end portion 466 of the second tube member 462. As such, the first tube member 460 pushes the compression members 468 radially inward toward the elastic strand 304. In turn, the compression member 468 exert pressure on the elastic strand 304 until the upstream end portion 352 becomes captured between the compression members 468. Thus, the one-way snare 400 prevents the upstream end portion 352 of the broken elastic strand 304 from retracting further upstream in the manufacturing process.

It is to be appreciated that the snare apparatuses here in can be configured to operate in different ways. For example, the third embodiment shown in FIGS. 8A-8E may be configured such that advancement of the stretched elastic strand 304 through the second tube member 462 does not force the compression members 468 radially outward. Rather, once the elastic strand 304 breaks, the retraction of the upstream end portion 352 and loss of stretch in the elastic strand 304 causes the cross sectional area of the elastic strand to increase, which in turn, forces the compression members radially outward.

This application is a continuation of Ser. No. 14/162,863, filed on Jan. 24, 2014, which claims the benefit of U.S. Provisional Application No. 61/764,111, filed on Feb. 13, 2013, the entireties of which are incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A one way snare apparatus for isolating a broken elastic strand, the apparatus comprising:
    a housing;
    a snare member connected with the housing, wherein the snare member is movable relative to the housing between a first position and a second position, wherein the snare member is movable in a first direction from the second position to the first position, and wherein the snare member is movable in a second direction from the first position to the second position;
    wherein the housing comprises a first tube member, and the snare member comprises a second tube member telescopically received within the first tube member;
    wherein when the snare member is in the first position, the snare member permits advancement of a continuous elastic strand in the first direction; and
    wherein when the snare member is in the second position, the snare member prevents an end portion of a broken elastic strand from retracting in the second direction through the housing, wherein the second direction is opposite the first direction.

2. The apparatus of claim 1, wherein the second tube member includes an end portion having an outer diameter, OD, defined by a plurality of compression members.

3. The apparatus of claim 2, wherein the first tube member defines an inner diameter, ID, wherein the outer diameter, OD, of the end portion of the second tube member is larger than the ID.

4. An apparatus for isolating a broken elastic strand, the apparatus comprising:
    a housing;
    a snare member movably connected with the housing, the snare member movable between a first position and a second position, wherein the snare member is telescopically received within the housing;
    a pathway extending through the housing adapted to receive an advancing elastic strand;
    wherein the pathway is relatively wide when the snare member is in the first position; and
    wherein the pathway is relatively narrow when the snare member is in the second position.

5. A method for isolating broken strands of elastic with a one way snare comprising a housing and a snare member movably connected with the housing, wherein the snare member is telescopically received within the housing, and wherein the housing defines an inner diameter and the snare member includes an end portion that defines an outer diameter larger than the inner diameter of the housing, the method comprising the steps of:
    advancing an elastic strand in a first direction through the housing and through the snare member;
    placing the snare member in a first position;
    separating the elastic strand in the first direction to create an upstream end portion and a downstream end portion;
    retracting the upstream end portion in a second direction toward the housing, wherein the second direction is opposite the first direction; and
    capturing the upstream end portion by moving the snare member in the second direction to a second position and compressing the end portion of the snare member with the housing.

* * * * *